United States Patent [19]

Eisenmenger et al.

[11] Patent Number: 5,010,248

[45] Date of Patent: Apr. 23, 1991

[54] SAMPLING HYDROPHONE

[76] Inventors: Wolfgang Eisenmenger, Landhausstrasse 7, D-7140 Ludwigsburg; Joachim Staudenraus, Bruehlstrasse 45, D-7303 Neuhausen, both of Fed. Rep. of Germany

[21] Appl. No.: 411,479

[22] PCT Filed: Jan. 17, 1989

[86] PCT No.: PCT/EP89/00053
§ 371 Date: Nov. 24, 1989
§ 102(e) Date: Nov. 24, 1989

[87] PCT Pub. No.: WO89/06512
PCT Pub. Date: Jul. 27, 1989

[30] Foreign Application Priority Data

Jan. 25, 1988 [DE] Fed. Rep. of Germany ....... 3802024

[51] Int. Cl.$^5$ .............................................. H01J 5/16
[52] U.S. Cl. ........................... 250/227.21; 250/231.19; 367/141
[58] Field of Search .................. 250/227.19, 227.21, 250/227.27, 231.19; 356/131, 132, 133; 367/149, 141; 73/655, 656, 657

[56] References Cited

U.S. PATENT DOCUMENTS

| | | | |
|---|---|---|---|
| 3,917,410 | 11/1975 | Ulrich | 356/133 |
| 4,162,397 | 7/1979 | Bucaro | 250/199 |
| 4,235,113 | 11/1980 | Carome | 73/655 |
| 4,487,206 | 12/1984 | Aagard | 128/667 |
| 4,599,711 | 7/1986 | Cuomo | 367/141 |
| 4,691,709 | 9/1987 | Cohen | 128/667 |
| 4,907,878 | 3/1990 | Arditty | 356/133 |

FOREIGN PATENT DOCUMENTS 3302089  4/1986  Fed. Rep. of Germany.
2089032  6/1982  United Kingdom.

*Primary Examiner*—David C. Nelms
*Attorney, Agent, or Firm*—Ralf H. Siegemund

[57] ABSTRACT

An optical reflection hydrophone probe is described for determining the pressure time sequence of pressure waves in liquids. In such a hydrophone probe one end of an optical waveguide (glass fiber) dips into the liquid. The reflection of light at the end of the glass fiber is ties, through the relation between the index of refraction and density, to the pressure amplitude in the liquid. The optical reflection hydrophone probe permits acquisition of pressure signals which are vey steep such as shockwaves and amplitudes, for long use life of the probe and for an extremely high ratio of safety against interference.

12 Claims, 1 Drawing Sheet

SAMPLING HYDROPHONE

DESCRIPTION OF THE INVENTION

Hydrophone probes are use for investigating and characterizing water acoustic signals such as ultrasonic pulses or shockwaves as far as their spatial, temporal shape is concerned. Known are particular piezoelectric hydrophone probes under utilization of crystalline ceramic or polymeric piezoelectric material whereby the sensitive element has either planar or spherical shape contours are is situated at the end of a usually coaxial electrical connection. A description of new developments in this particular area is found in the journal Acoustica, volume 54, 1983, page 23.

The aim for developing a hydrophone probe is to replicate acoustic signals with as few errors and as few feedbacks as possible, in a very sensitive fashion and for maximum temporal and spatial resolution. In addition, in the case of shockwave investigations there is a requirement for a high use life in the pressure range of about 1 kbar as arising in the focal point of medical shockwave devices. This is in addition to the requirement for as large as possible a distance or spacing between the actually sensitive tip of the probe and the electronic equipment to be connected thereto such as an amplifier. The last mentioned requirement follows from the point of view of medicine when shockwave pressure is to be determined within the body of the human being.

The presently available piezoelectric hydrophone probes attain a bandwidth of about 10 megaHertz with a sensitivity of about 1 mV per bar. This is described in Acoustica, volume 54, page 23, 1986 and also in volume 64, 1987, page 85. On the other hand shockwave signals have a bandwidth of to 1 gigaHz, see e.g. Acoustica, volume 14, page 187, 1964. In the case of a bandwidth of 10 MHz the effective sampling diameter of the probe is about 1/10 mm. Since the sampling tip is constructed from several layers such as the inner electrode, a piezoelectric layer and an outer electrode further reduction in the dimensions of the device for purposes of increasing the bandwidth encounters considerable difficulties. The sensitivity of the probe goes down with decreasing sampling surface. In addition a large feed length would cause considerable loss in sensitivity owing to the inherent cable capacity. Owing to the aforementioned layer configuration of these probes the use life is quite limited in the case of shockwave investigations. In the pressure range from about 1 kbar and in the case of a fully developed shockwave front the use life is quite frequently below a hundred shockwave exposures.

It is an object of the present invention to provide a hydrophone probe having a very simple configuration and having effective dimensions with diameters below 1/10 mm for purposes of increasing the bandwidth, without loss in sensitivity so that for shockwave exposure in the 1 kbar range one still obtains a high use life, and whereby the feeder length is freely selectable without loss in sensitivity. Moreover these hydrophone probes should be easy to calibrate and have a high degree of reproducibility. This object is attained in accordance with with the invention as per the characterizing feature of claim 1.

Hence instead of a piezoelectric hydrophone probes a light conductor having the configuration of a glass or polymer fiber is introduced into the acoustic wavefield, and the temporal variation of the light reflection at the boundary or interface at the end of the light conductor vis-a-vis the liquid is used as a hydrophone signal during the temporal pressure change. The light reflection at the light conductor end face is tied to the pressure amplitude in the liquid through a relationship between the index of refraction and the density. Upon a pressure increase the density also rises and therefore the index of refraction of the liquid increases accordingly. Such a relationship basically exists also for the light conductor material itself whereby however the lower compressibility of the solid light conductor material as compared with liquid, any pressure dependent changes in the index of reflection of the liquid prevails over such changes in the solid. The changes of the reflection of light is photoelectrical registered through the temporal intensity distribution of reflected light for known light incidence.

Further configurations are indicated in the dependent claims.

Since the light reflection is effective only at the end face of the light conductor that is e.g. at the interface of the glass or synthetic fiber with the liquid, the effective thickness of the probe in relation to the light conductor wavelength and the probe diameter is limited to the optical thickness of the fiber itself.

The measuring method can also be implied for turpid liquids e.g. if the immediate environment of the probe is established by an optically perfect liquid contained e.g. in a balloon. The balloon filled liquid may also be replaced by a suitable optically interference free rubber elastic or solid body such as plexiglass or polyurethane. This way makes it possible to use the probe in the medical area e.g. for measuring shockwaves in the interior of the human body through a catheter or in conjunction with endoscopic methods.

For optimizing the sensitivity of the probe and in order to optimize also the linearity of the indication it is of advantage to select appropriately the index of reflection of the liquid or of the body having the high quality or the index of refraction of the light conductor.

In addition one may establish a particularly strong pressure dependency of the index of refraction through suitable selection of the light frequency e.g. at the flank of the molecular oscillation or electronic transition and through the resulting pressure shift of the corresponding optical transition, by means of which the sensitivity is increased considerably. In the visible and ultraviolet spectral range the liquid may attain favorable properties through the adding of dye molecules. The corresponding feasibility also exists for doping light wave conductors either a glass fiber or synthetic fiber with atoms or molecules which do show a strong pressure dependency of the index of refraction and therefore of the light reflection.

Also the limit angle for total reflection is controlled through the pressure induced changes in the index of refraction. For an optical radiation rate in the light conductor with preference in the total reflection angle one can make the influence of that angle prevail over the entire reflected light intensity.

The kind of surface effective at the light conductor end and for attaining reflection can be selected in various ways. For once a planar polished surface is suitable. A planar surface of good optical quality however can also be produced through a slight scratching and break-off. Also one may provide for a semispherical or spherical end of the light conductor and e.g. through melting of the end so as to establish an ideal surface configurations whereby for all the light angles of the wave conductor one establishes a perpendicular limit angle of incidence and this makes possible single computation for calibration purposes.

A particular simple powerful optical measuring device for acquiring reflection and its conversion into a pressure signal is established through a continuous mode laser of a high power output up to 1 watt and with coupling of the laser energy through an optical coupler and a photodiode amplification for measuring the reflected light density. In order to consider amplitude variations in the primary laser beam, a directly branched off laser signal portion may be compared e.g. through subtraction with the sampled signal. This laser signal component moreover can be used for controlling the laser intensity towards a constant level. All in all the invention offers the following advantages over the state of the art.

Conventionally available glass fiber types or polymer fibers can be used as optical waveguides. The several surfaces that are alone sensitive can be produced through fracture or polishing. The effective sample diameters can be smaller than 1/10 mm. The sensitive volume is formed by the fiber diameter and half of the wavelength. On perpendicular pressure wave incidence in water this corresponds to a maximum bandwidth of up to 30 gigaHz. The diameter and length of the waveguide have no direct influence on the sensitivity. Therefore small diameters for producing large bandwidths do not offer any problems even in the case of lateral incidence such as an ideal spherical characteristic as well as large lengths e.g. for employment in the medical field. This is in contrast to problems posed by known piezoelectric hydrophone probes. The sensitivity is just limited by the photon noise which, depending on the input light power, can be drastically reduced. The interference of all other noise components in the light source can be reduced either through comparative methods or by way of control. Electrical interference e.g. resulting from the spark discharge in the case of shockwave production are screened owing to the ideal isolation provided by the glass fiber. Also the use life is considerably higher particularly for measuring shockwaves owing to the mare simpler configuration as compared with piezoelectric hydrophones. Also in the case of damage to the glass fiber end a new glass fiber surface can very easily be made. All in all the optical reflection sampling hydrophone has therefore a number of important advantages over the known piezoelectric hydrophone probes.

BRIEF DESCRIPTION OF THE INVENTION

Figure 3A:
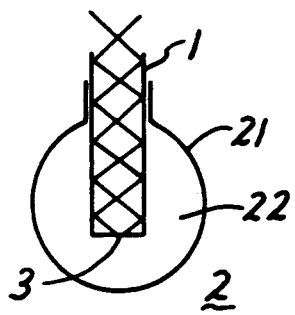
Figure 3B:
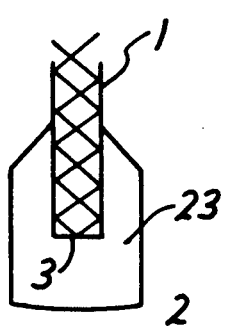
Figure 3C:
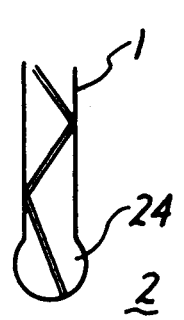

FIGS. 3a, 3b and 3c describe three light conductor configurations.

Figure 1:
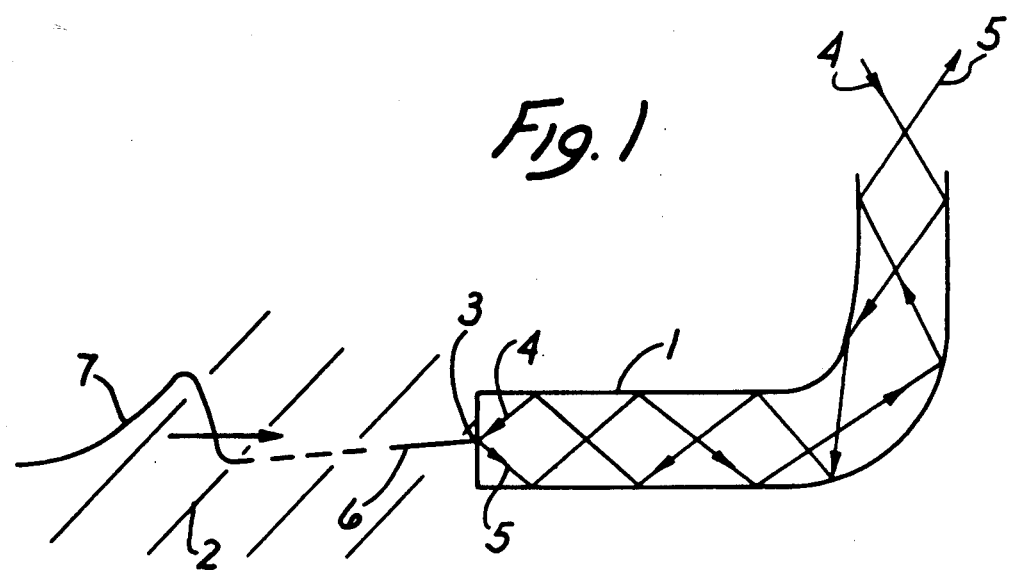
FIG. 1 illustrates the action of a pressure wave on a light conductor.
Figure 2:
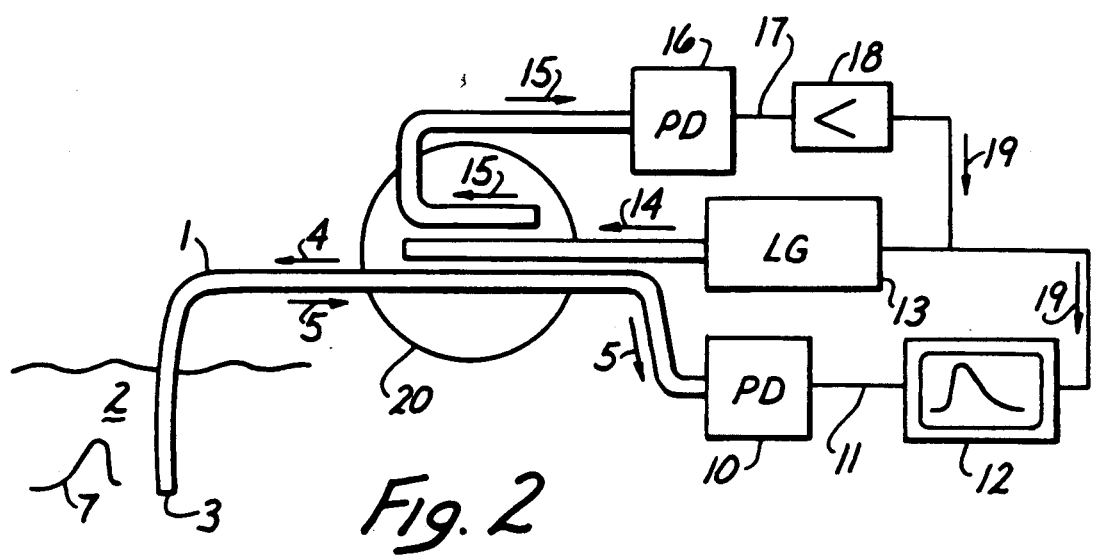
FIG. 2 illustrates a detection system according to the invention.

FIG. 1 illustrates a glass fiber 1 dipping or being immersed in liquid 2 and having a reflecting end surface 3. The incident light 4 is passed through the light conductor to the boundary 3 and is partially reflected and partially transmitted (6) into the liquid. Owing to a pressure wave 7 the liquid 2 is compressed right in front of the boundary surface 3 so that for a short period of time the index of refraction in the Liquid increases which reduces the intensity of the reflected light 5. The reflected light 5 is converted in a photodetector 10 (FIG. 2) into an electrical signal 11 and registered through an oscilloscope 12. FIGS. 3a, b, c show different configurations for the light conductor end in the liquid 2. In the case of FIG. 3a a balloon 21 envelops the light conductor end 3 the balloon being filled with an optical high quality liquid 22. This embodiment is recommended for use in light impermeable or a turpid acoustic medium 2. In this case one may alternatively use a configuration as per FIG. 3b wherein an optically clear e.g. rubber elastic body or any other synthetic body 23 circumscribes the light conductor end 3. In FIG. 3c the end 24 of the light conductor 1 is provided in spherical form. This way the reflected surface will prevail in the case of perpendicular light incidence. On the side of the light signal production and processing an optical coupler 20 splits light 14 from the light generator 13 being a laser into a measuring branch 4 and a reference branch 15. The signal production from the measuring light 4 up to the imaging in the oscilloscope 12 was already described. On the other hand the comparing light 15 is used in a photocell 16 and converted into an electrical comparing signal 17 and amplified in the amplifier 18 to be used as a control signal 19 for reducing the laser noise. The reference signal 19 is subtracted in the oscillograph 12 from the measuring signal 11 for similar rest or zero level adjustment. Also there is a constant level control of the laser signal 14 by means of the reference signal 19 serving as control input.

We claim:

1. Hydrophone probe for measuring pressure amplitudes in a liquid medium (2) comprising, a light conductor in the form of an optical waveguide (1) having one end situated in the liquid medium; means connected on opposite end of the waveguide to be responsive to changes in the degree of reflection of light at the boundary 3 of said end and of liquid adjacent said end of the light conductor on account of pressure dependent changes in the relative index of refraction at said boundary and with reference to the liquid medium for being indicative of variable pressure amplitudes in said liquid medium, said means further including an optical reflection measuring device having a large temporal resolution sufficient to respond to pressure variations beyond a megahertz range.

2. Hydrophone probe in accordance with claim 1, the light conductor end which is situated in the liquid, being surrounded by a balloon (21) filled with a liquid (22) of high optic quality.

3. Hydrophone probe in accordance with claim 1, the light conductor being situated in the liquid and being surrounded by a body made of a solid, for example a rubber elastic material of high optic quality.

4. Hydrophone probe in accordance with claim 1 further including means tuned to a light frequency corresponding to a molecule transition or a molecular relaxation of the surrounding liquid or of the body or of the light conductor.

5. Hydrophone probe in accordance with claim 1 said connected means responding to pressure depending changes in the boundary angle of total reflection, and producing an output signal representative thereof.

6. Hydrophone probe in accordance with claim 1, the end the light conductor being polished.

7. Hydrophone probe in accordance with claim 1 the end (3) of the light conductor (1) being a planar fracture or cleavage surface.

8. Hydrophone probe in accordance with claim 1 characterized in that the end of the light conductor 1 is spherically shaped (24).

9. Hydrophone probe in accordance with claim 1 further including a light source and first means (14) for coupling the incident light of the light source 13 to said waveguide; and the connected means including a photodetector (10) being connected to the waveguide for acquiring a light signal therefrom.

10. Hydrophone probe in accordance with claim 9 including means for branching off a part of the light required for the measuring device, from the light source (13), and as a branch off signal and feeding it to another photodetector 16 with amplifier 18; and means for comparing this branched off signal as amplified with said signal provided by said photodetector (10).

11. Hydrophone probe in accordance with claim 10, and means connected to receive said branched off signal used in addition, and further connected to the light source for controlling the light intensity of the requisite light as provided by the source, towards a constant level.

12. Hydrophone probe for measuring a pressure amplitude in a liquid medium comprising a light conductor having one end immersed in the liquid, and having an end face;
   transparent optical means surrounding the end and being compressed upon an increase in pressure in the surrounding liquid, the optical means having an index of refraction that varies with pressure;
   light source means for coupling light into the conductor for reflection at said end;
   circuit means including photo detection means responding to the reflection such that pressure changes at said end face change the effective index of refraction and thereby change a relative proportion of reflection of reflected light.

* * * * *